(12) United States Patent
Geier et al.

(10) Patent No.: US 7,897,794 B2
(45) Date of Patent: Mar. 1, 2011

(54) METHOD FOR PURIFYING HYDROXYMETHYLFURFURAL USING NON-FUNCTIONAL POLYMERIC RESINS

(75) Inventors: Douglas F. Geier, Decatur, IL (US); John Glenn Soper, Mt. Zion, IL (US)

(73) Assignee: Archer Daniels Midland Company, Decatur, IL (US)

( * ) Notice: Subject to any disclaimer, the term of this patent is extended or adjusted under 35 U.S.C. 154(b) by 356 days.

(21) Appl. No.: 12/213,317

(22) Filed: Jun. 18, 2008

(65) Prior Publication Data

US 2009/0018352 A1 Jan. 15, 2009

Related U.S. Application Data

(60) Provisional application No. 60/944,629, filed on Jun. 18, 2007.

(51) Int. Cl.
*C07D 307/46* (2006.01)
(52) U.S. Cl. .......................................... 549/488
(58) Field of Classification Search .................. 549/488
See application file for complete search history.

(56) References Cited

U.S. PATENT DOCUMENTS

| | | | |
|---|---|---|---|
| 2,750,394 | A | 6/1956 | Peniston |
| 2,929,823 | A | 3/1960 | Garber et al. |
| 4,339,387 | A | 7/1982 | Fleche et al. |
| 4,590,283 | A | 5/1986 | Gaset et al. |
| 5,893,947 | A | 4/1999 | Pease et al. |
| 6,441,202 | B1 | 8/2002 | Lightner |
| 6,706,192 | B2 | 3/2004 | Keri |
| 2002/0123636 | A1 | 9/2002 | Lightner |
| 2006/0128977 | A1 | 6/2006 | Sanborn et al. |
| 2006/0142599 | A1 | 6/2006 | Sanborn |
| 2006/0199892 | A1 | 9/2006 | Podszun et al. |

FOREIGN PATENT DOCUMENTS

GB 600871 4/1948

OTHER PUBLICATIONS

Román-Leshkov, Y., et al., "Phase Modifiers Promote Efficient Production of Hydroxymethylfurfural from Fructose", Science, Jun. 30, 2006, pp. 1933-1937, vol. 312, www.sciencemag.org.
Lewkowski, J., "Synthesis, chemistry and applications of 5-hydroxymethylfurfural and its derivatives", General Papers ARKIVOC, 2001, pp. 17-54, ARKAT USA, Inc.
Google Search Results for LWEATIT, Jan. 11, 2007, http://www.google.com.
International Search Report issued in Patent Application No. PCT/US08/67367 dated on Sep. 8, 2008.
Notification Concerning Transmittal of International Preliminary Report on Patentability issued in International Patent Application No. PCT/US2008/067367 filed Jun. 18, 2008.

*Primary Examiner* — Bernard Dentz
(74) *Attorney, Agent, or Firm* — Mark W. Roberts (57) ABSTRACT

Disclosed are methods of at least partially purifying HMF from an aqueous mixture containing reactants and products of HMF synthesis from fructose that relies on use of non-functional polymeric resins. A first type of non-functional polymeric resin preferentially adsorbs HMF relative to fructose and is used to remove a majority of fructose from the reaction mixture. HMF is desorbed from the first non-functional polymeric resin with an organic solvent such as acetone. A second type of non-functional polymeric resin preferential adsorbs furfural from an aqueous reaction mixture allowing HMF to pass through. In one embodiment, these non-functional polymeric resins may be used alone in combination with each other to obtain HMF of high purity. In other embodiments, one or more of the foregoing non-functional polymeric resin resins is used in combination with cation exchange chromatography to still further purify the HMF.

20 Claims, 9 Drawing Sheets

METHOD FOR PURIFYING HYDROXYMETHYLFURFURAL USING NON-FUNCTIONAL POLYMERIC RESINS

CROSS REFERENCE TO RELATED APPLICATION

This application is based upon and claims the benefit of priority from U.S. Provisional Patent Application No. 60/944,629 filed on Jun. 18, 2007, the entire contents of which are incorporated by reference herein.

FIELD OF THE INVENTION

Technical Field

This disclosure relates to a method for purifying hydroxymethylfurfural. More particularly, this disclosure relates to a method for purifying hydroxymethylfurfural which involves adsorption and desorption of an aqueous mixture containing components of a hydroxymethylfurfural synthesis mixture through one or more non-functional polymeric resins, in certain cases optionally followed by chromatographic-separation over a cation exchange resin.

INTRODUCTION

A major product in the acid-catalyzed dehydration of fructose is 2-hydroxymethyl-5-furfuraldehyde, also known as hydroxymethylfurfural which is abbreviated, HMF. The structure of HMF is shown below:

Hydroxymethylfurfural

HMF has been reported to have antibacterial and anticorrosive properties. HMF is also a key component, as either a starting material or intermediate, in the synthesis of a wide variety of compounds, such as furfuryl dialcohols, dialdehydes, esters, ethers, halides and dicarboxylic acids. One example of a dicarboxylic acid that can be derived from HMF is levulinic acid. An important reaction of HMF is the organic oxidation to 2,5-furandicarboxylic acid, a compound that has been suggested for use as a monomer in the production of plastics. HMF is also currently under investigation as a treatment for sickle cell anemia. In short, HMF is an important chemical compound and a method of synthesis on a large scale to produce HMF absent significant amounts of impurities, side products and remaining starting material has been sought for nearly a century.

One method for the synthesis of HMF comprises passing an aqueous fructose solution through a thermal flow-through reactor to obtain a mixture of unreacted fructose and HMF. By this method, further reactions such as condensation, rehydration, reversion and other rearrangements may occur, resulting in a plethora of unwanted side products. It is desirable to remove the side products which may interfere with the purification of HMF. One such side product, humin, is a brown to black, fluffy solid which is almost completely insoluble in water, base, acids and organic solvents of all types. It coats the sides of reaction vessels and serves as an efficient thermal insulator, thereby causing poor heat transfer. Humin also induces emulsification of the aqueous phase with various extraction solvents, thereby further complicating the recovery of HMF.

Generally, the reaction mixture also contains an organic solvent that extracts HMF from the aqueous phase. However, although the extraction step may remove some of the HMF, there still remains a significant amount of HMF in the aqueous phase, which also contains the unreacted fructose and other impurities, such as humin. In order to increase the yield of the reaction, it is desirable to remove the HMF from the aqueous phase.

Several techniques for the purification of HMF from aqueous solutions are known. British Patent No. 600,871 describes a method of manufacturing HMF in an autoclave at 130-230° C. The HMF is recovered from the aqueous reaction mixture by extraction with a suitable organic solvent such as ethyl acetate. U.S. Pat. No. 2,929,823 describes producing HMF from aqueous sugar solutions at temperatures from 250° to 380° C. using very short reaction times, on the order of 0.1 to 180 seconds. The HMF is extracted into an organic solvent, such as furfural, water immiscible alcohols, ketones, ethers, esters and halogenated hydrocarbons or mixtures thereof. The organic solvent may be added to the aqueous reaction mixture during the reaction or after the reaction.

Another method for the production of HMF from fructose involves the conversion of aqueous fructose solutions of from 10 to 50 wt % in a two-phase reactor system in which the aqueous fructose solution is combined with either DMSO (dimethyl sulfoxide) or PVP (polyvinylpyrrolidone). The HMF is purified by continuous extraction into an organic phase, such as methylisobutylketone, 2-butanol, or a mixture thereof.

However, one drawback associated with the above mentioned methods is that fructose and low molecular weight humin are also extracted into the organic phase. Accordingly, the purity of the HMF derived from these methods is questionable.

Another two-phase procedure is described in DE-OS No. 30 33 527. Here, under temperatures below 100° C., fructose containing aqueous solutions are decomposed with acid ion-exchange resins, in the presence of an organic water-immiscible solvent able to dissolve HMF. However, one problem with this procedure is the necessity to use a large surplus of the organic solvent, about 7:1 volumetric ratio, as compared to the aqueous phase, requiring high cost to remove the solvents and the generation of excessive waste.

To overcome the above mentioned problems, U.S. Pat. No. 4,740,605 describes a method for purifying HMF by eluting the aqueous reaction mixture of HMF, fructose and side products through an ion-exchange resin and fractionating the eluent. However, some of the fractions contain mixtures of fructose and HMF, which must be subsequently eluted on other columns in order to increase the yield of HMF from the reaction mixture.

In summary, in most known methods for synthesizing HMF from fructose, a large amount of fructose remains in the post reaction aqueous layer. Accordingly, due to the problems associated with separating relatively small amounts of HMF compared to amount of fructose present, it remains difficult to obtain high purity HMF. There is a need therefore, for a method of purifying HMF from aqueous reaction mixtures that eliminates or reduces the above cited problems.

SUMMARY OF THE DISCLOSURE

In order to overcome the above mentioned problems, the disclosure provides a method of purifying HMF from an aqueous reaction mixture by using at least two columns, at least one of which contains a non-functional resin that preferentially adsorbs HMF. In different embodiments, the second column may contain either a strong acid cation exchange resin or a different non-functional polymeric resin that preferentially adsorbs furfural. The order of use is not important, however, the examples illustrate using the HMF adsorbing non-functional polymeric resin first when the second resin is a cation exchange resin, and using the furfural adsorbing non-functional polymeric resin first when two non-functional polymeric resin are used in sequence. In either case, fructose is removed from the aqueous mixture by contacting the aqueous mixture on a column containing a non-functional polymeric resin that adsorbs HMF, and then washing the column with water to remove the fructose.

In one general embodiment, there is disclosed methods of at least partially purifying HMF from a mixture containing reactants and products of HMF synthesis from fructose that includes: contacting a first non-functional polymeric resin that preferentially adsorbs HMF relative to fructose with an aqueous solution containing the mixture of reactants and products of HMF synthesis for a time sufficient to adsorb a majority of HMF from the mixture onto the non-functional polymeric resin; contacting the non-functional polymeric resin with water until a majority of fructose from the mixture is removed from the non-functional polymeric resin while a majority of the HMF from the mixture remains adsorbed to the non-functional polymeric resin; contacting the non-functional polymeric resin with an organic solvent in an amount sufficient to desorb the majority of HMF from the non-functional polymeric resin; and collecting the desorbed HMF in a first eluted solution containing the organic solvent.

In one exemplary case, HMF is eluted from such a column with acetone, the acetone is removed, redissolved in an aqueous solvent, and the HMF is then further purified from contaminating side products by contacting with the second, cation exchange column, which is eluted with water to chromatographically separate the components.

In another general embodiment, there is disclosed a method of at least partially purifying HMF from a mixture containing reactants and products of HMF synthesis from fructose, that includes: contacting a first non-functional polymeric resin that preferentially absorbs furfural relative to HMF with an aqueous solvent containing the mixture of reactants and products of HMF synthesis for a time sufficient to adsorb a majority of furfural from the mixture onto the first non-functional polymeric resin; contacting the first non-functional polymeric resin with a flow of water until a majority of HMF and fructose from the mixture is removed from the non-functional polymeric resin in a first fraction while a majority of the furfural from the mixture remains adsorbed to the non-functional polymeric resin, and collecting the first fraction; contacting a second non-functional polymeric resin that preferentially adsorbs HMF relative to fructose with the first fraction for a time sufficient to adsorb a majority of HMF from the first fraction onto the second non-functional polymeric resin; contacting the second non-functional polymeric resin with water until a majority of fructose from the first fraction is removed from the second non-functional polymeric resin while a majority of the HMF from the mixture remains adsorbed to the second non-functional polymeric resin; and contacting the second non-functional polymeric resin with an organic solvent in an amount sufficient to desorb the majority of HMF from the second non-functional polymeric resin and collecting the desorbed HMF in a first eluted solution containing the organic solvent;

In certain exemplary embodiments, the first non-functional polymeric resin that preferentially adsorbs HMF is Lewatit® S7768.

In certain exemplary embodiments and the second cation exchange resin is a strongly acidic resin selected from the group consisting of Finex® CS13GC293 and Mitsubishi® UBK555.

In another exemplary embodiment, where two non-functional polymeric resins are used, the first or second non-functional polymeric resin that preferentially adsorbs furfural is Lewatit® VPOC1064.

One advantage of the methods described herein lies in the removal of the fructose from the aqueous mixture before the fractionation of the remaining components of the aqueous mixture to remove any other impurities that may be present, for example, humin polymer materials.

Another advantage is that the methods using two non-functional polymeric resins yield a product of high purity with substantial reduction in furfural using inexpensive materials in a two step procedure.

DETAILED DESCRIPTION OF THE DISCLOSURE

Prior to describing the present invention in detail, certain terms that have meanings generally understood by those of ordinary skill in the art are nevertheless defined herein to better distinguish nuances in meaning that may apply to different embodiments of the invention. It is understood that the definitions provided herein are intended to encompass the ordinary meaning understood in the art without limitation, unless such a meaning would be incompatible with the definitions provided herein, in which case the provided definitions control.

"Chromatographic Separation" and variations thereof refers to rate-based separation of chemical species over a stationary solid phase chromatographic sorbent material by differential partitioning of the species between the stationary phase and a mobile eluent phase. Accordingly, chromatographic separation can be accomplished by the use of single mobile phase without a requirement to change eluent conditions. In this regard, chromatographic separation may be characterized as a "continuous separation process" because the species being separated are in continuous motion.

"Adsorptive/Desorptive Separation" or "Adsorptive/Desorptive Chromatography" and variations thereof are specifically meant to distinguish from chromatographic separation, and refers to a process where chemical species are separated by immobilizing one species on a solid phase sorbent while moving another species preferentially with the eluent under a first eluent condition, then changing eluent conditions to a second condition where the immobilized species is desorbed from the sorbent to preferentially partition with the eluent. Accordingly, the two features that fundamentally distinguish chromatographic separation from adsorptive/desorptive separation are that in the latter case (i) a first eluent condition is selected to accomplish, as near as possible, complete immobilization of at least one species on the chromatographic material, and (ii) there is a change to a second eluent condition selected to cause the immobilized species to become mobile. In this regard, adsorptive/desorptive separation may be characterized as a "discontinuous" or "stepwise" separation process.

The ordinarily skilled person will recognize that depending on eluent selection and chemical species, the same solid phase chromatographic material may be used to accomplish chromatographic separation, adsorptive/desorptive separation, or both. For example, in a first step to separate a mixture containing species A, B and C, an ion exchange material may be employed as a sorbent stationary phase in conjunction with an eluent at a first pH selected to cause species A and B to be immobilized on the sorbent while species C preferentially partitions with the mobile eluent phase thereby accomplishing adsorptive/desorptive separation of species A and B from species C. In a second step, the eluent conditions can be changed to a second pH that causes species A and B to preferentially partition with the moving phase. If the change in pH also causes species A and B to differentially partition between the mobile phase and the stationary phase, then species A and B will move at different rates over the stationary phase and be chromatographically separated on the same ion exchange material.

"Non-functional polymeric resin" means a polymeric backbone material such as polystyrene, that itself has no organic functional groups other than CC, C=C, and CH bonds, that has been cross linked to form a porous matrix, and which has not been derivatized to include any additional organic or inorganic moieties. One characteristic of non-functional polymeric resins is that they are non reactive and contain no ionic or otherwise solvatable species of molecules that would form hydrogen bonds or ionic bonds in an aqueous environment. Hence, the only molecular interaction between molecules in contact with non-functional polymeric resins is by van der Waals forces.

Turning now to the present discovery, HMF is typically synthesized from fructose, by dehydration in the presence of an acid catalyst. Although several solvent systems may be used for the reaction, the most economical solvent is water even though the use of water rather than an organic solvent increases the occurrence to unwanted reaction products such as furfural, polymeric forms of HMF and/or furfurals (humins-detected in the samples as "color bodies" or "subjective color") and miscellaneous degradation products. Also, under typical aqueous conditions the reaction does not go to completion because with excess water the reaction occurs in reverse and in equilibrium, a significant amount of rehydration occurs so typically a large amount of fructose remains in the reaction mixture. Hence, the reactants and products of HMF synthesis will minimally include fructose and HMF and likely also include furfural and humins.

Typically in the past, purification of HMF from reactants and other products has relied on distillation and/or biphasic liquid extraction or on cation exchange chromatographic separation. As disclosed herein, it has been surprisingly discovered than non-functional polymeric resins are highly effective in separating HMF from other reactants and products of HMF synthesis. Because the principle reactants and products of HMF synthesis, fructose, furfural, HMF and humins are similar in size and polarity, it is surprising that these species would have substantially different abilities to be adsorbed to non-functional polymeric resins. Moreover, generally, non-functional polymeric resins are not suited to separation of major components, like HMF and fructose, from reaction mixtures, but rather are typically used to remove trace impurities. However, in one preferred embodiment of the present disclosure, it was found that the non-functional resin, Lewatit®S7768, is ideally suited for separating a majority of fructose from HMF and other side products without the need for extensive fractionation. Depending upon the concentration of HMF, several bed volumes of the aqueous mixture of HMF may be loaded on the column, before washing the column with eluent, to remove the fructose while leaving the HMF on the column. The eluent on the first column may be any solvent that allows fructose to elute from the resin while not eluting HMF. In one embodiment, the first eluent is deionized water, although other solutions such as aqueous solutions of inorganic salts, organic salts and buffer materials may be used for the first eluent.

In fact, it has been discovered that HMF in an aqueous solution can be nearly quantitatively adsorbed to certain non-functional polymeric resins while fructose and furfural substantially flow through such resins without adsorption. After adsorption, the HMF can be desorbed from the non-functional polymeric resin by contacting with organic solvents, especially low molecular weight polar solvents such as acetone, ethanol, a propanol, ethyl acetate, butanol, amyl alcohol, isopentyl alcohol, and mixtures thereof, such as fusel oils, which is a mixture of the low molecular weight polar organic solvents that are obtained from distilling ethanol from a fermentation broth. In certain practices the polar organic solvent is water miscible, such as ethanol, acetone, propanols, acetonitrile, dimethyl formamide, etc. In an exemplary practice, the polar organic solvent is acetone.

One example of a non-functional polymeric resin that preferentially adsorbs HMF is Lewatit® S7768 (Lanxess Sybron Chemicals Inc, Birmingham, N.J.). This resin is generally characterized as neutral, highly crosslinked polystyrene beads with a mean diameter of about 0.44 to 0.55 mm, a mixed pore diameter of about 0.5 to 10 nm, a pore volume of about 0.6 to 0.8 ml per gram, a surface area of greater than 1300 square meters per gram, and a water retention capacity of about 38-45%.

It also has been discovered that other non-functional polymeric resins can preferentially adsorb furfural from an aqueous mixture of reactants and products of HMF synthesis, while permitting fructose and HMF to flow through without substantial adsorption. One example of such a non-functional polymeric resin that preferentially adsorbs furfural is Lewatit® VPOC1064, also available from Lanxess. This resin is characterized as macroporous neutral cross linked polystyrene beads of a more uniform size, with a mean diameter of about 0.5+/−0.05 mm, a more uniform pore diameter of about 5-10 nm, a pore volume of about 1.2 ml per gram, a surface area of about 800 square meters per gram, and a water retention capacity of about 50-60%. Furfural can be desorbed from such resins to regenerate the resin for further use by desorption with the same type of organic solvents used to elute HMF from the other class of non-functional polymeric resin resins, then washing with water.

Other resins that fit into one of the categories of either preferential HMF or furfural adsorption include, but are not limited to Amberlite XAD-4, XAD-1180, and XAD-16 (Rohm & Haas Chemicals LLC, Elgin Ill.), Diaion HP20, HP21, SP70 and SP850 (Mitsubishi Chemical Company, Tokyo, Japan). It is not presently understood which characteristic or combination of characteristics of these and similar non-functional polymeric resins confer the ability to preferentially bind HMF or furfural, however, one of ordinary skill in the art can use the guidance of the present examples provided herein after to empirically determine which species will be adsorbed by executing the straight forward pulse tests described therein.

It further has been discovered that using the above type of resins used alone together, or combined with cationic exchange chromatography, typically using a strongly acidic resin such as one with a sulfonate functional group, provides an effective and economical method for substantial purification of HMF from other reactants and products of HMF synthesis.

Figure 1:
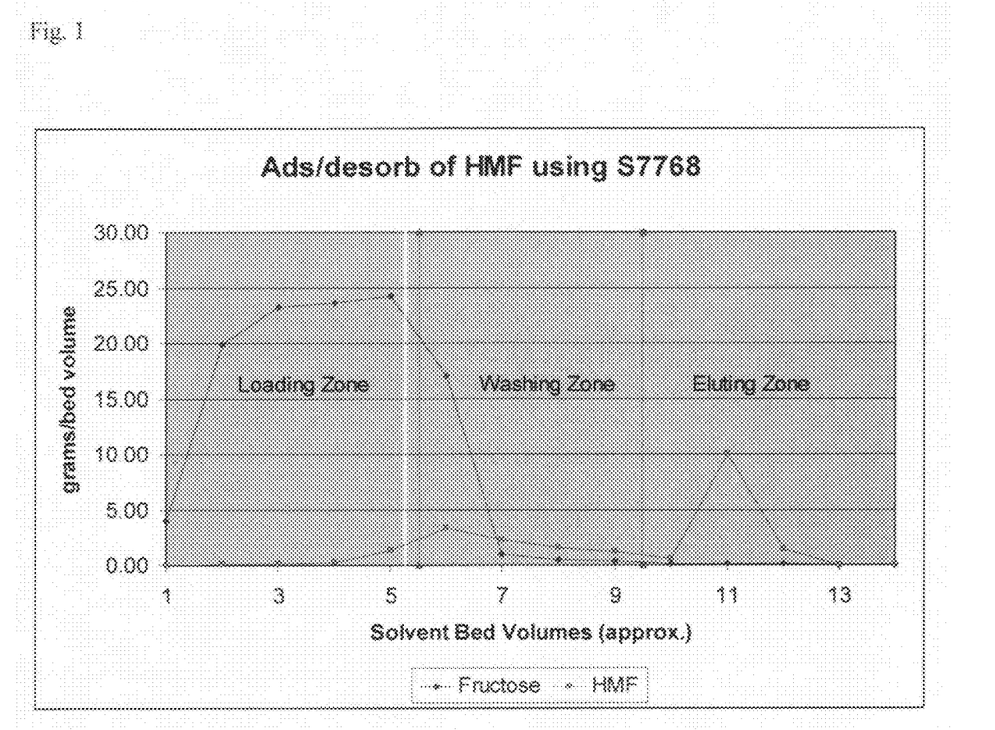
FIG. 1 is a graph showing the HPLC analysis of the fractions collected from a non-functional polymeric resin column that preferentially adsorbs HMF used in Example 1.

In typical examples of using a combination of a non-functional polymeric resin for HMF adsorption followed by cation exchange chromatographic separation, a reaction mixture from an HMF synthesis in water is loaded onto a first non-functional polymeric resin that preferentially adsorbs HMF. The resin is washed with water and a majority of fructose passes through the resin with the initial load and wash, while a majority of the HMF remains adsorbed. The HMF is then desorbed and eluted from the non-functional polymeric resin with an organic solvent. FIG. 1 depicts adsorption/desorption of HMF using such a non-functional polymeric resin. It is desirable to use a low boiling point solvent such as acetone as the desorbing eluent, because in one typical practice, the organic solvent is removed from HMF enriched eluent by evaporation or distillation.

Figure 6:
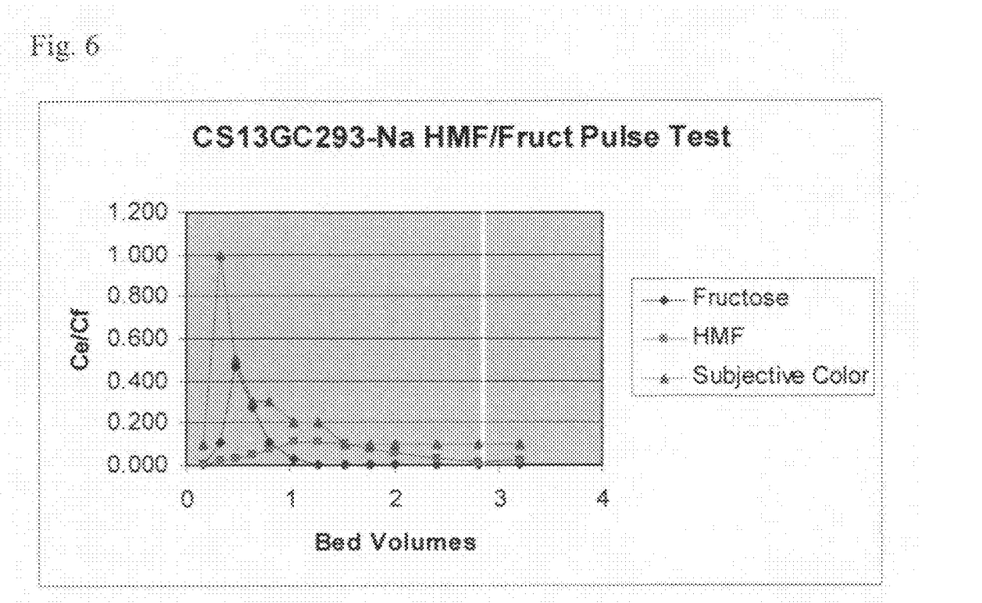
FIG. 6 is a graph showing the HPLC analysis of the fractions collected from the cation exchange column used in Example 6.
Figure 7:
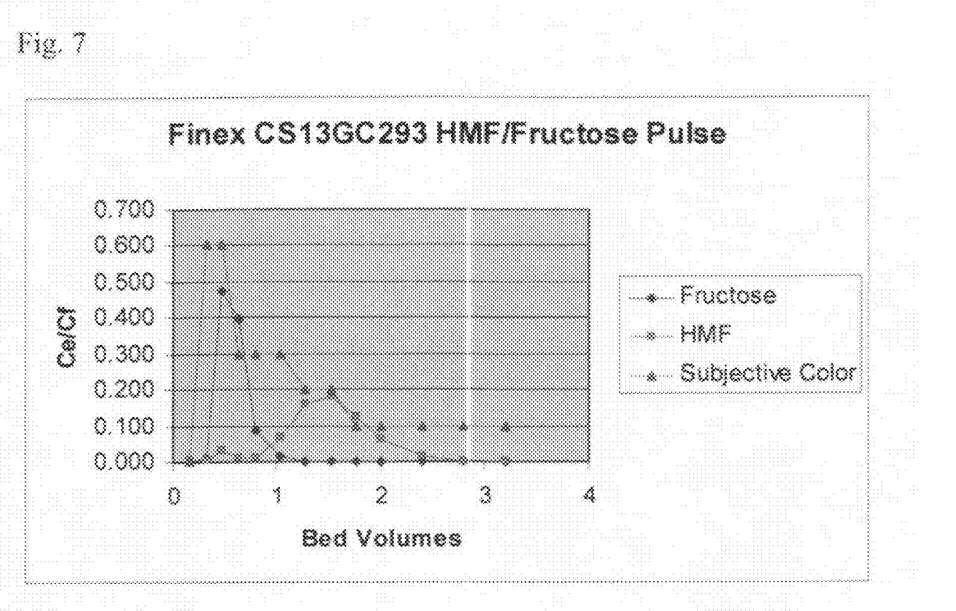
FIG. 7 is a graph showing the HPLC analysis of the fractions collected from the cation exchange column used in Example 7.
Figure 8:
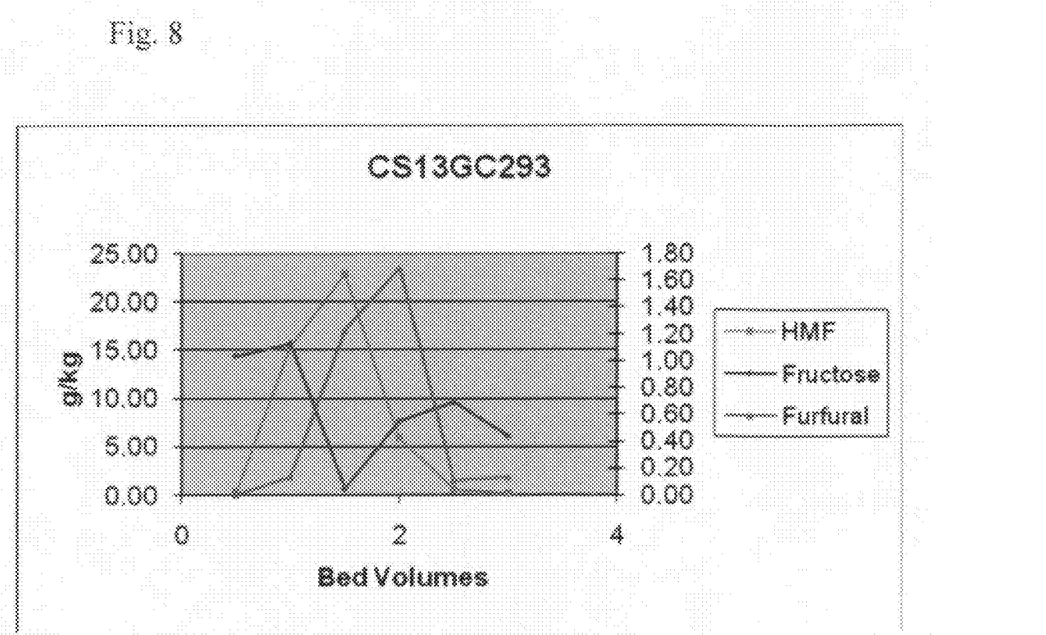
FIG. 8 is a graph showing the HPLC analysis of the fractions collected from a cation exchange column after first adsorbing and desorbing HMF on a first non-functional polymeric resin column.

The remaining residue, which is oily or solid and typically contains residual water, is then dissolved in an aqueous solvent and loaded onto the cation exchange resin. The same aqueous solvent is typically used as the mobile phase to effect the chromatographic separation over the cation exchange resin. The aqueous solvent may be water alone, or water with an appropriate salt, e.g., as $CaCl_2$, NaCl, etc, selected to optimize the chromatographic separation. The cation exchange resin, typically loaded in a column, is prepared by being equilibrated with the same aqueous solvent. As illustrated in FIGS. 2-7, which depict cation exchange chromatography of a whole HMF synthesis reaction mixture that has not been pre-treated by adsorption and desorption of HMF, humins (subjective color) typically begins eluting first, followed by fructose then HMF. FIG. 8 illustrates an example where the HMF reaction mixture is first adsorbed and desorbed from the non-functional polymeric resin then subsequently separated by cation exchange chromotography. In this case, there is much less residual fructose in the feed, and it elutes in two peaks, one initially in the flow-through and another after the peak of HMF begins elution. Furfural also begins eluting after the HMF so for best purity a cut is made to take the mid fraction (e.g. 0.5 to 1.5 bed volumes in FIG. 8) where the HMF is most separated from furfural and fructose. The HMF may then be crystallized by methods known to those skilled in the art.

As an alternative to removing the organic solvent prior to redissolving the HMF in water prior to the cation exchange chromatography, it is also possible to omit the evaporation step and simply mix the organic solvent containing the eluted HMF with an appropriate amount of aqueous solvent and to perform the cation exchange chromatography in the mixed solvent system. In this case it is most preferable to use a polar organic solvent that is miscible with water, such as acetone, ethanol, or a propanol as the HMF solvent and the mobile phase. Although this mixed solvent embodiment of chromatography can be effective, in certain instances, it may not be desirable if a substantial amount of humins remain in the feed because the organic solvent lowers the effectiveness of the cation exchange separation of humins from HMF.

Figure 9:
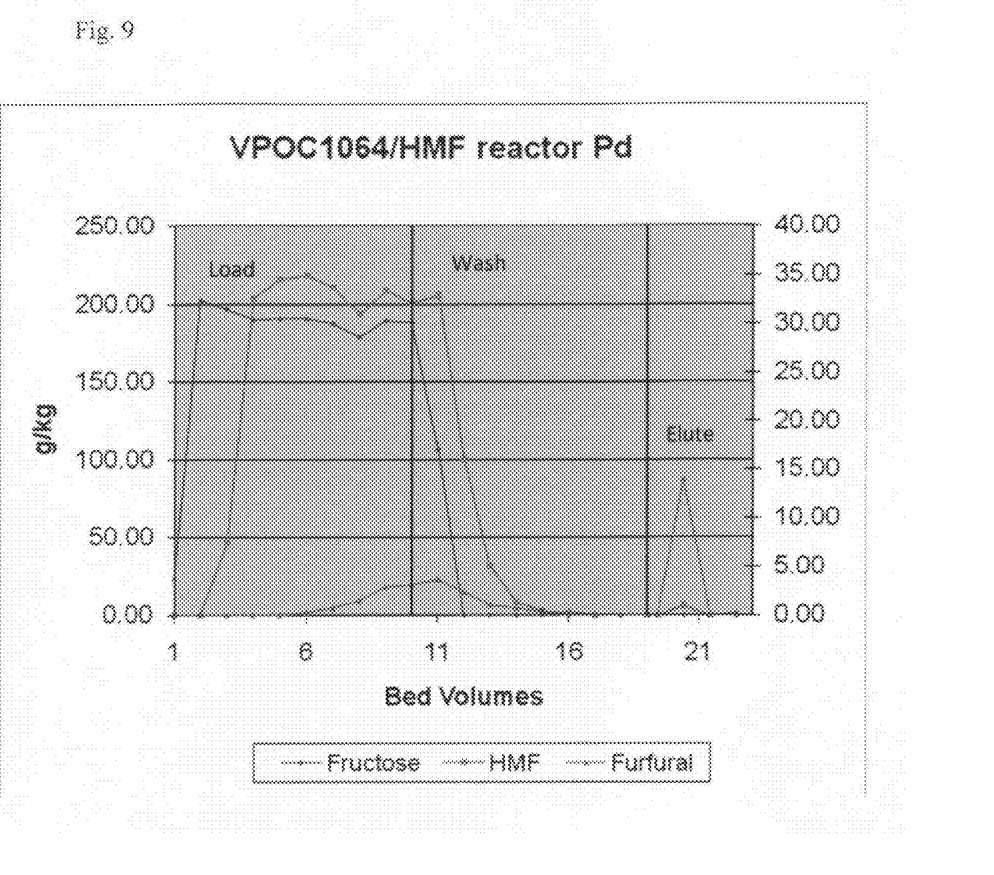
FIG. 9 is a graph showing the HPLC analysis of the fractions collected from a non-functional polymeric resin that preferentially adsorbs furfural.

In typical embodiments of using a combination of two different non-functional polymeric resins, the cation exchange chromatographic separation can be omitted altogether. In one step, a mixture of the HMF synthesis reaction in water is loaded onto a non-functional polymeric resin such as Lewatit® VPOC1064 that preferentially binds furfural (and some humins). HMF and fructose elute in the flow-through and wash, which are combined and immediately loaded onto a different non-functional polymeric resin such as Lewatit® S7768 that preferentially adsorbs HMF allowing the fructose to pass through. The HMF is then eluted with acetone and the acetone removed by evaporation or distillation to obtain a fraction of highly purified HMF. The adsorption of furfural on Lewatit® VPOC1064 is illustrated in FIG. 9. Furfural may also be eluted with acetone when using a VPOC1064 packed column.

The use of the two different non-functional polymeric resins can also be done in reverse, i.e., the HMF adsorbing resin can be used to first remove fructose, then the HMF and any remaining furfural eluted in the organic solvent can be loaded in an aqueous solvent after removal of the organic solvent, and the furfural can be removed by adsorption on non-functional polymeric resin that preferentially binds furfural, with the HMF passing though in the flow-through and wash. Afterwards, the resin may be washed with aqueous solvent so as to be regenerated for further use.

Although in typical practices it is not necessary to use cation exchange chromatography when two different non-functional polymeric resins are used in combination, in certain particular practices it may desirable to use all three types of resins in various combinations to purify HMF. For example, as illustrated in FIG. 9, where a HMF adsorbing resin Lewatit® S7768 was used first to obtain an HMF enriched fraction with reduced fructose content and followed by chromatography on a Finex CS13GC293 cation exchange resin to separate furfural and residual sucrose from HMF, the peaks of furfural and HMF nevertheless have some overlap. To obtain a more highly enriched HMF fraction of about 82% purity, it was necessary to take the sample representing 0.5 to 1.5 bed volumes of eluent to reduce the furfural content. If higher yield were desired, it would be beneficial to take the fractions representing 0.5 to 2 bed volumes, however that fractionation would result in excess furfural. The excess furfural could be removed by subsequent chromatography on the Lewatit® VPOC1064 to adsorb the excess furfural and still obtain high recovery of the HMF in the flow-though.

In embodiments using a combination with cation exchange chromatography, preferably the resin is a strong acid cation exchange resin. In particular examples, the resin is Finex® CS13GC293, Mitsubishi® UBK555, or a similar type resin. Strong acid cation-exchange resins are synthetic resins containing an active functional group, such as sulfonic, carboxylic, benzoic, or other acidic groups, that give the resin the property of combining with and thereby exchanging cations between the resin and a mobile phase solution. The cation exchange resins may be conditioned to the desired form in any manner known in the art. For example, if the acid form of the ion-exchange resin is preferred, the resin may be conditioned with an aqueous solution of 5% hydrochloric acid. For the calcium form of the resin, conditioning may be performed with, for example, a 5% aqueous solution of calcium chloride or another suitable calcium salt. For the sodium form of the resin, conditioning may be performed with, for example, a 5% solution of sodium hydroxide, or another suitable sodium salt. The conditioning of the column should be performed with an amount of solution containing an excess of ions adequate to convert substantially all of the resin to the desired form. For example, in one embodiment, five bed volumes of aqueous 5 wt/vol % calcium chloride solution were passed through the column to condition it. Then, after conditioning the column, the column is washed with deionized water to remove excess conditioning solution.

Figure 2:
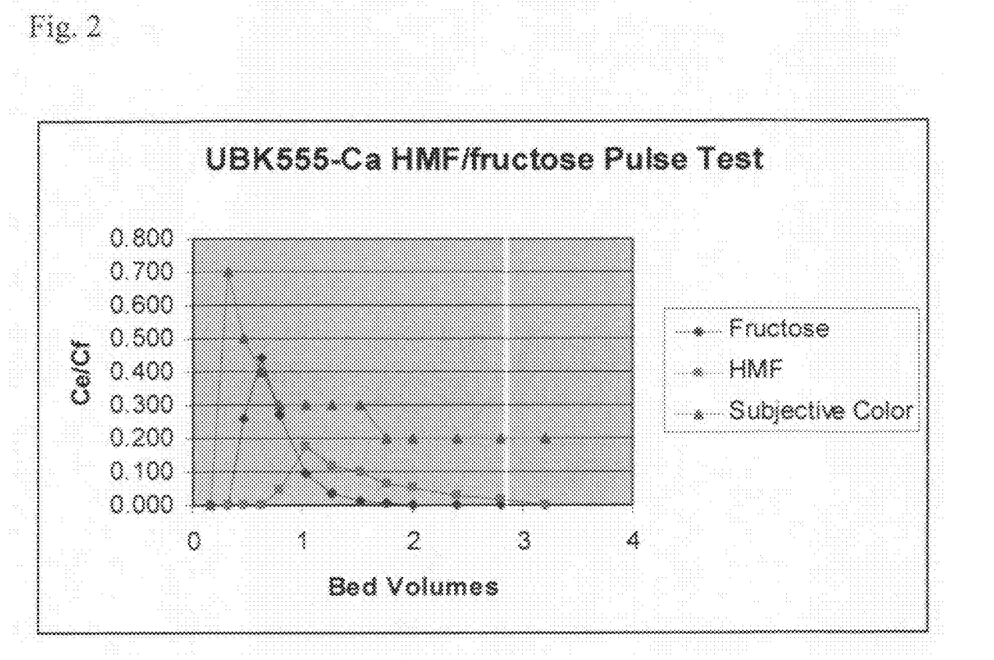
FIG. 2 is a graph showing the HPLC analysis of the fractions collected from the cation exchange column used in Example 2.
Figure 5:
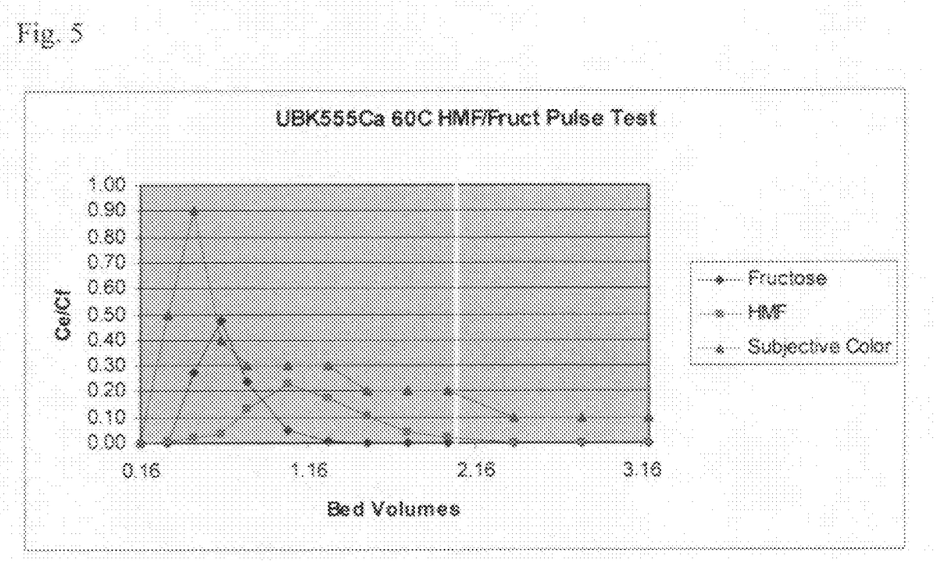
FIG. 5 is a graph showing the HPLC analysis of the fractions collected from the cation exchange column used in Example 5.

The aqueous mixture is loaded onto the cation exchange column followed by elution with a suitable eluent. The eluent may be any solvent that has the property of allowing HMF to be separated via chromatography from the other materials present in the aqueous mixture. In one preferred embodiment, deionized water is used, although the eluent may also be an aqueous solution of inorganic salts, organic salts, or buffer materials or an aqueous solution intermixed with a miscible organic solvent. The flow rate of the eluent may be adjusted to optimize the separation of the HMF from the other materials. Depending on the size of the column and sample, the flow rate may be from about 1 ml/minute to about 50 ml/minute, preferably from about 2 ml/minute to about 20 ml/minute. In the examples, the flow rate was about 5 ml/minute to about 15 ml/minute. The temperature for elution may be any temperature suitable to optimize the separation of materials. Generally, the temperature is from about 15° C. to about 75° C., and preferably from about 20° C. to about 60° C. As illustrated in FIG. 5, chromatography at a higher temperature of about 60° C. resulted in detectably better separation than at room temperature under similar conditions as depicted in FIG. 2. Gravity or pressure may be used to adjust the flow rate of the column.

The following examples are intended to illustrate the present discovery using illustrative resins and conditions and are not intended to be limiting. One of ordinary skill in art can use other resins and conditions to accomplish similar or improved separations by routine experimentation.

EXAMPLES

Adsorption/Desorption of HMF Over the First, Non-Functional Polymeric Resin

Example 1

A 15 mm inner diameter×600 mm glass column is loaded with 100 ml Lewatit® S7768 resin. The resin is then conditioned by passing three bed volumes of 5 wt/vol % aqueous sodium hydroxide through the column, followed by 5 bed volumes of deionized water. The flow rate used through out the entire procedure is 5 ml/minute. Then, five bed volumes of aqueous mixture containing 40 g/kg HMF, 200 g/kg fructose and other unknown amounts of materials are loaded on the column. After elution of the aqueous mixture, four bed volumes of deionized water is then contacted with the column, followed by 5 bed volumes of acetone.

The analysis of the fractions collected from this first step of the reaction is shown in FIG. 1. As can be seen, the fraction collected after a total of 11 bed volumes contains no fructose, only HMF. Furthermore, all of the fructose appears to have been removed from the column before the HMF began eluting off.

Examples 2-7

Chromatography Over the Second Cation Exchange Resin

Example 2

A 15 mm inner diameter×600 mm glass column was loaded with 100 ml Mitsubishi® UBK555 ion-exchange resin. The resin was conditioned by passing five bed volumes of 5 wt/vol % calcium chloride in deionized water through the column followed by washing the column with five bed volumes of deionized water. The water was then brought to the top of the resin bed and 15 ml of aqueous reaction mixture containing 40 g/kg HMF, 200 g/kg fructose and other side products was added to the top of the column. The mixture was allowed to sink to the top level of the resin bed by opening the column exhaust valve. Then 2 ml of deionized water was added to the column, allowed to sink into the resin bed to the level of the top of the resin bed. Then 5 ml of deionized water was added to the top of the column. The column was closed and eluted with a deionized water stream at a flow rate of 10 ml/minute at 60° C. temperature. Fractions were taken every 0.8 minutes. A total of 3.16 bed volumes of eluent was eluted from the column. HPLC was used to analyze the fractions taken from the column. The results are shown in FIG. 2.

Example 3

Figure 3:
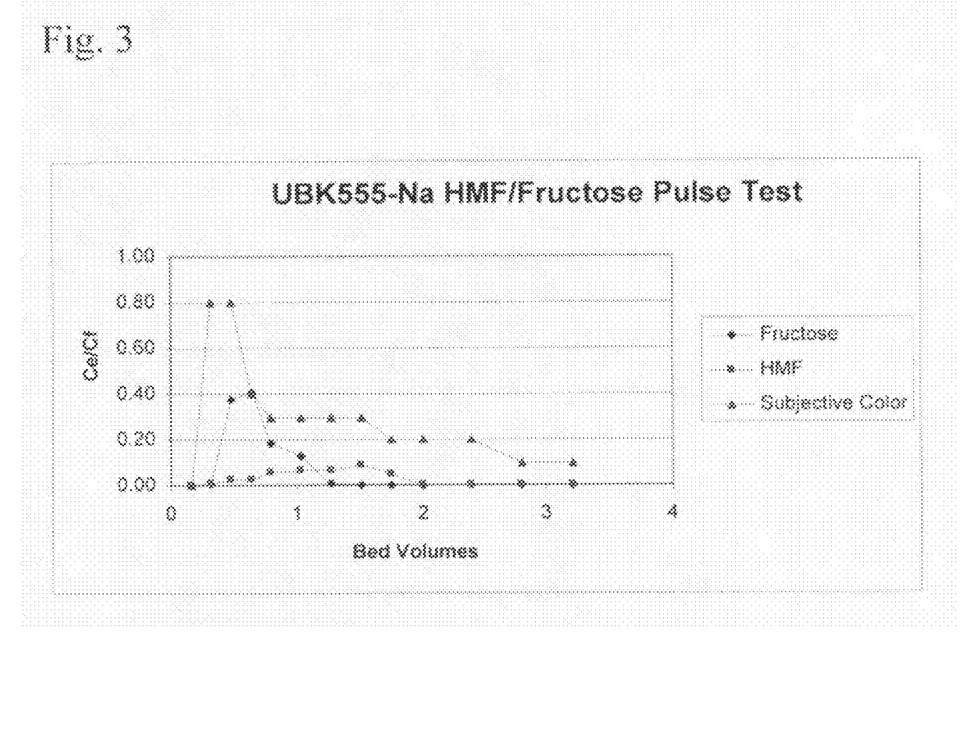
FIG. 3 is a graph showing the HPLC analysis of the fractions collected from the cation exchange column used in Example 3.

The conditions and equipment used in Example 3 are the same as that described in Example 2 except that the column was conditioned with 5 wt/vol % sodium hydroxide. The results are shown in FIG. 3.

Example 4

Figure 4:
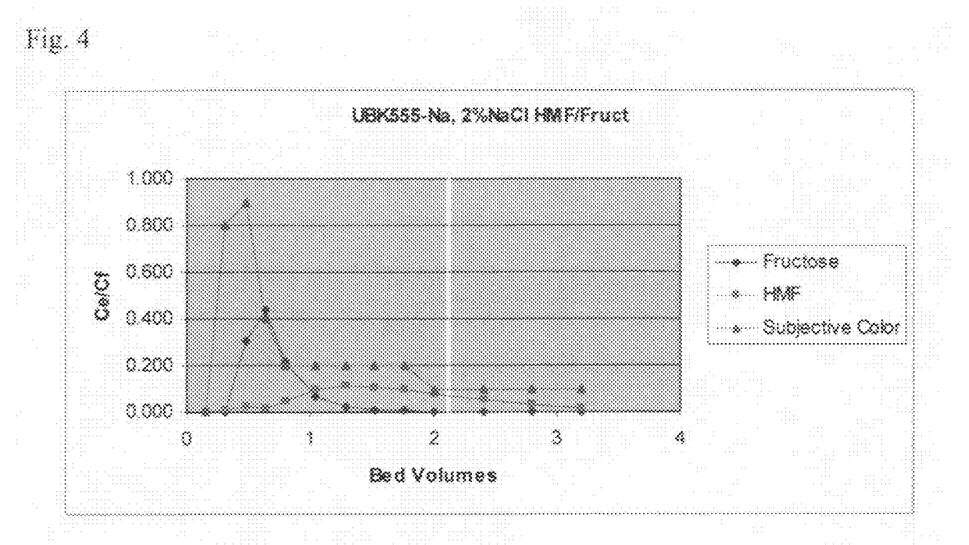
FIG. 4 is a graph showing the HPLC analysis of the fractions collected from the cation exchange column used in Example 4.

The conditions and equipment used in Example 4 are the same as that described in Example 2 except that the column was conditioned with 5 wt/vol % sodium hydroxide, and 2% NaCl in deionized water was used as the third eluent. The results are shown in FIG. 4.

Example 5

The conditions and equipment used in Example 5 are the same as that described in Example 2 except that the temperature of the column was 60° C. The results are shown in FIG. 5.

Example 6

The conditions and equipment used in Example 6 are the same as that described in Example 2 except that the column was conditioned with 5 wt/vol % sodium hydroxide and the resin used was Finex CS13GC293 ion-exchange resin. The results are shown in FIG. 6.

Example 7

The conditions and equipment used in Example 3 are the same as that described in Example 6 except that the column was conditioned with 5 wt/vol % hydrochloric acid. The results are shown in FIG. 7.

Examples 2-7 represent the elution through the second column described in the above steps for purification of HMF. As can be seen from each of the Graphs 2-7, the subjective color, which represents the presence of humin and other colored impurities present in the reaction mixture, is to a large extent removed from the column before the HMF begins to be eluted from the column. Thus, the HMF is purified significantly by this process. However, to increase the yield of HMF recovered, a preferred method is to use the first column from Example 1 and the second column from one of Examples 2-7 in series, as described in Example 8.

Adsorption on First, Non-Functional Polymeric Resin Followed by Chromatographic Separation on Second, Cation Exchange Column Example 8

A 15 mm inner diameter×600 mm glass first column is loaded with 100 ml Lewatit® S7768 resin. The resin is then conditioned by passing three bed volumes of 5 wt/vol % aqueous sodium hydroxide through the first column, followed by 5 bed volumes of deionized water. The flow rate for the first column is 5 ml/minute. Then, five bed volumes of a first aqueous mixture containing 40 g/kg HMF, 200 g/kg fructose and other unknown amounts of materials are loaded on the first column. After the first aqueous mixture has contacted the column, four bed volumes of deionized water is then contacted with the first column, followed by 5 bed volumes of acetone. The acetone fraction is then collected and concentrated in vacuo to yield a residue containing HMF and side products. The residue is then dissolved in 15 ml of deionized water to form a second aqueous mixture containing HMF and the side products.

A 15 mm inner diameter×600 mm glass second column is loaded with 100 ml Mitsubishi® UBK555 ion-exchange resin, the "second resin". The second resin is conditioned by passing five bed volumes of 5 wt/vol % calcium chloride in deionized water through the second column followed by washing the second column with five bed volumes of deionized water. The water is then brought to the top of the resin bed and 15 ml of the second aqueous reaction mixture is added to the top of the second column. The mixture is allowed to sink to the top level of the second resin bed by opening the column exhaust valve. Then 2 ml of deionized water is added to the second column, allowed to sink into the second resin bed to the level of the top of the second resin bed. Five ml of deionized water is then added to the top of the second column. The second column is closed and eluted with a deionized water stream at a flow rate of 10 ml/minute at a temperature of 25° C. Fractions are taken every 0.8 minutes. A total of 3.16 bed volumes of eluent is eluted from the second column. HPLC is used to analyze the fractions taken from the second column to obtain substantially pure HMF.

Example 9

396 grams of an aqueous mixture containing 15.3% HMF on a solids basis (fructose, HMF, and furfural) was passed through a column of Lewatit® S7768, followed by washing with approximately 2.5 bed volumes (BV) of deionized water. 107.5 grams of HMF enriched product was recovered by eluting with acetone. The product contained 82.9% HMF on a solids basis. The acetone was removed using a rotary evaporator resulting in about 40 milliliters of an orange residue containing HMF, water and other materials. A portion of this residue (5.6 grams) containing 2.2 grams of HMF was further dissolved in water and then passed through a column of Finex CS13GC293 cation resin in the acid form, using water as the mobile elution phase. Eluted fractions starting at 0.5 bed volumes (BV) and finishing at 1.5 BV were collected and shown to contain 1.72 grams of HMF. This final product was 94.0% HMF on a solids basis with a yield of 78.2% for the cation exchange chromatography step. FIG. 8 illustrates this cation exchange purification step used directly after the S7768 non-functional polymeric resin purification step.

Adsorption of Furfural on First, Non-Functional Polymeric Resin and Adsorption of HMF on Second, Non-Functional Polymeric Resin Example 10

About 1044 grams of feed comprising aqueous phase of reaction components of HMF synthesis was passed through a 100 ml Levatit VPOC1064 column (15 mm ID×600 mm) that was subsequently washed with water. This feed contained about 193 grams of fructose, 33 grams of HMF, and 3.9 grams of furfural. A cut of the flow-through and wash fractions representing bed volumes 3 through 6, which contained fructose and HMF in water that passed through the VPOC1064 resin without substantial adsorption, were pooled and shown to contain 72.1 grams of fructose, 10.6 grams of HMF with no detectable furfural. Furfural adsorbed to the column was eluted with acetone. FIG. 9 illustrates the adsorption and elution of furfural from the Levatit VPOC1064 resin along with the bed volumes of flow-through fractions containing fructose and HMF.

This cut pool was used as a feed for adsorption and elution of HMF on the Levatit S7768 resin in a column. The feed was loaded onto the column and washed with water substantially as in Example 1. The non-adsorbing load fractions immediately eluting from the column and with the wash were pooled and shown to contain 71.7 grams of fructose and about 0.4 grams of HMF. After the wash, the resin was eluted with acetone substantially as in Example 1. The combined acetone eluent was shown to contain 10.2 grams of HMF and 0.2 grams of fructose. The HMF purity on a total solids basis was 99.1%.

We claim:

1. A method of purifying HMF from a mixture containing reactants and products of HMF synthesis from fructose, comprising, contacting a first non-functional polymeric resin that preferentially adsorbs HMF relative to fructose with an aqueous solution containing the mixture of reactants and products of HMF synthesis for a time sufficient to adsorb a majority of HMF from the mixture onto the non-functional polymeric resin;

contacting the first non-functional polymeric resin with water until a majority of fructose from the mixture is removed from the non-functional polymeric resin while a majority of the HMF from the mixture remains adsorbed to the non-functional polymeric resin;

contacting the first non-functional polymeric resin with an organic solvent in an amount sufficient to desorb the majority of HMF from the non-functional polymeric resin; and collecting the desorbed HMF in a first eluted solution containing the organic solvent.

2. The method of claim 1 wherein the HMF from the first eluted solution is further purified by contacting the HMF obtained from the first eluted solution with a chromatography resin different from the first non-functional polymeric resin and eluting the chromatography resin to obtain a fraction containing further purified HMF.

3. The method of claim 2 wherein further purifying the HMF comprises, removing the organic solvent from the first eluted solution and obtaining a residue of partially purified HMF;

dissolving the residue of partially purified HMF in an aqueous solvent to obtain a second aqueous solution comprising HMF;

contacting an acidic ion exchange polymeric resin with the second aqueous solution comprising HMF; and chromatographically separating at least a majority of HMF from other components in the second aqueous solution by eluting the acidic ion exchange polymeric resin with an aqueous mobile phase and collecting a second eluted solution containing the further purified HMF.

4. The method of claim 3 wherein the second eluted solution containing the HMF is still further purified by contacting a second non-functional polymeric resin that preferentially adsorbs furfural relative to HMF with the second eluted solution and eluting the second non-functional polymeric resin with an aqueous mobile phase to obtain a fraction containing the still further purified HMF.

5. The method of claim 1 wherein the organic solvent is at least one selected from the group consisting of acetone, ethanol, a propanol, ethyl acetate, butanol, amyl alcohol, isopentyl alcohol, and fusel oils.

6. The method of claim 1 wherein the organic solvent is at least one water miscible organic solvent.

7. The method of claim 1 wherein the organic solvent is acetone.

8. The method of claim 6 wherein the HMF from the first eluted solution is further purified by:

mixing an aqueous solvent with the first eluted solution containing the organic solvent to obtain a mixed solution of the partially purified HMF;

contacting an acidic cation exchange polymeric resin with the mixed solution of the partially purified HMF; and chromatographically separating at least a majority of HMF from other components in the mixed solution of the partially purified HMF by eluting the cation exchange polymeric resin with a mobile phase comprising water and the water miscible organic solvent in the same proportion as the mixed solution and collecting a second eluted solution containing the further purified HMF.

9. The method of claim 8 wherein the water miscible organic solvent is acetone.

10. A method of purifying HMF from a mixture containing reactants and products of HMF synthesis from fructose, comprising, contacting a first non-functional polymeric resin that preferentially absorbs furfural relative to HMF with a first aqueous solvent containing the mixture of reactants and products of HMF synthesis for a time sufficient to adsorb a majority of furfural from the mixture onto the first non-functional polymeric resin;

contacting the first non-functional polymeric resin with a flow of a second aqueous solvent until a majority of HMF and fructose from the mixture passes through the non-functional polymeric resin in a first fraction while a majority of the furfural from the mixture remains adsorbed to the non-functional polymeric resin, and collecting the first fraction;

contacting a second non-functional polymeric resin that preferentially adsorbs HMF relative to fructose with the first fraction for a time sufficient to adsorb a majority of HMF from the first fraction onto the second non-functional polymeric resin;

contacting the second non-functional polymeric resin with a third aqueous solvent until a majority of fructose from the first fraction is removed from the second non-functional polymeric resin while a majority of the HMF from the mixture remains adsorbed to the second non-functional polymeric resin; and contacting the second non-functional polymeric resin with an organic solvent in an amount sufficient to desorb the majority of HMF from the second non-functional polymeric resin and collecting the desorbed HMF in a second eluted solution containing the organic solvent.

11. The method of claim 10 further comprising removing the organic solvent from the second eluted solution and obtaining a residue of at least partially purified HMF.

12. The method of claim 10 wherein at least two of the first, second and third aqueous solvents are the same.

13. The method of claim 10 wherein at least one of the first, second and third aqueous solvents is water.

14. The method of claim 10 further comprising removing the organic solvent from the second eluted solution to obtain a residue of at least partially purified HMF dissolving the residue of at least partially purified HMF in a fourth aqueous solvent to obtain a partially purified aqueous solution comprising HMF;

contacting a strong ion exchange polymeric resin with the partially purified aqueous solution comprising HMF; and chromatographically separating at least a majority of HMF from other components in the partially purified aqueous solution comprising HMF by eluting the strong ion exchange polymeric resin with an aqueous mobile phase and collecting a fraction enriched with HMF.

15. The method of claim 10 wherein the first non-functional polymeric resin is contacted before the second non-functional polymeric resin.

16. The method of claim 10 wherein the second non-functional polymeric resin is contacted before the first non-functional polymeric resin.

17. The method of claim 10 wherein the first non-functional polymeric resin is in the form of polystyrene beads with a mean diameter of about 0.44 to 0.55 mm, a pore diameter of about 0.5 to 10 nm, a pore volume of about 0.6 to 0.8 ml per gram, a surface area of greater than 1300 square meters per gram, and a water retention capacity of about 38-45%.

18. The method of claim 10 wherein the second non-functional polymeric resin is in the form of cross linked polystyrene beads with a mean diameter of about 0.44 to 0.55 mm, a pore diameter of about 5-10 nm, a pore volume of about 1.2 ml per gram, a surface area of about 800 square meters per gram, and a water retention capacity of about 50-60%.

19. The method of claim 1 wherein the first non-functional polymeric resin that preferential adsorbs HMF is in the form of polystyrene beads with a mean diameter of about 0.44 to 0.55 mm, a pore diameter of about 0.5 to 10 nm, a pore volume of about 0.6 to 0.8 ml per gram, a surface area of greater than 1300 square meters per gram, and a water retention capacity of about 38-45%.

20. The method of claim 4 wherein the second non-functional polymeric resin is in the form of cross linked polystyrene beads with a mean diameter of about 0.44 to 0.55 mm, a pore diameter of about 5-10 nm, a pore volume of about 1.2 ml per gram, a surface area of about 800 square meters per gram, and a water retention capacity of about 50-60%.

* * * * *